United States Patent [19]
Barrett

[11] 3,961,188
[45] June 1, 1976

[54] HIGH INTENSITY RADIATION IMAGING SYSTEM

[75] Inventor: Harrison H. Barrett, Lexington, Mass.

[73] Assignee: Raytheon Company, Lexington, Mass.

[22] Filed: July 29, 1974

[21] Appl. No.: 492,815

Related U.S. Application Data

[62] Division of Ser. No. 250,224, May 4, 1972, Pat. No. 3,829,688.

[52] U.S. Cl. ............................. 250/303; 250/312; 250/323
[51] Int. Cl.² ..................................... G01T 1/161
[58] Field of Search ........... 250/510, 482, 369, 366, 250/367, 360, 358, 321, 320, 312, 303, 323

[56] References Cited
UNITED STATES PATENTS

| | | | |
|---|---|---|---|
| 1,164,987 | 12/1915 | Bucky | 250/320 |
| 2,730,566 | 1/1956 | Bartow et al. | 250/363 |
| 3,748,470 | 7/1973 | Barrett | 250/363 |
| 3,831,031 | 8/1974 | Barrett et al. | 250/363 |

*Primary Examiner*—Harold A. Dixon
*Attorney, Agent, or Firm*—David M. Warren; Joseph D. Pannone; Milton D. Bartlett

[57] ABSTRACT

A nuclear imaging system for mapping a spatially distributed source of high energy nuclear particles from a living organ which has selectively absorbed a radioactive compound in which the nuclear energy is spatially coded by a zone plate positioned between the source and a spatial detector, and a half tone screen is positioned between the source and the zone plate to increase the definition of the image.

5 Claims, 8 Drawing Figures

HIGH INTENSITY RADIATION IMAGING SYSTEM

CROSS REFERENCE TO RELATED APPLICATIONS

This is a division of application Ser. No. 250,224 filed May 4, 1972, now U.S. Pat. No. 3,829,688.

Application Ser. No. 77,459 entitled Imaging System Utilizing Spatial Coding, filed Oct. 2, 1970 by Harrison H. Barrett (now U.S. Pat. No. 3,748,470) and application Ser. No. 360,223 entitled Nuclear Imaging System, filed May 14, 1973 by Harrison H. Barrett and Frank A. Horrigan (now U.S. Pat. No. 3,825,757), which is a continuation of application Ser. No. 194,382 filed Nov. 1, 1971 (now abandoned), both assigned to the same assignee as this invention, are hereby incorporated herein by reference and made a part of this disclosure.

BACKGROUND OF THE INVENTION

Systems for determining the location and content of structures and/or organs in living bodies by detecting X-ray shadow of the body or by detecting high speed particles emanating from regions of the body which have selectively absorbed a radioactive compound require substantial exposure of the living body to potentially harmful radiation either by reason of the X-ray source being sufficiently intense and/or of long duration to produce a visual image on a film or from the concentration of the radioactive compound which must be absorbed by the body to emit a sufficient number of high energy particles to produce a useful image. In addition, when X-rays are used, the source of X-rays to produce good images requires that the area of the source be minimized to approach a point source so that when the X-rays were caused, for example, by a high speed electron stream, heating of the target limits the intensity and duration of the X-rays. Attempts to lessen the dosage of radiation to the living body by amplifying the image in the detector region are limited by noise considerations which show up in the final film as snow. In addition, the definition which can be achieved by such a process is limited.

Detection and recording of radiation carrying, as a spatial modulation thereof, image information is well known, such as the exposure of conventional films by light, by X-rays, or by other means; and in such systems, lenses, pinholes or collimators are normally used to form an image of the radiation source on the film or on an observation screen or on an electronic pickup device such as a vidicon camera tube. Such radiation from the object may be, for example, the result of reflection, direct radiation from the body due to its thermal temperature or radioactive content, conversion of incident radiation on the object to a different form of radiation as in the form of a fluorescent object, radiation from a body subject to nuclear energy bombardment, or an object heated by absorption of ligh and reradiation of the thermal energy in the infrared spectrum.

In copending application Ser. No. 360,223 (now U.S. Pat. No. 3,825,757), there is disclosed a coding system wherein a spatially distributed pattern of such energy may be coded with respect to a reference code by superimposing a spatially coded reference signal on the radiation pattern, thereby avoiding the need to use a phase coherent source of radiant energy to obtain a holographic form of the radiation pattern since the phase characteristics of the reference signal may be used for the subsequent decoding of the pattern to produce an image.

SUMMARY OF THE INVENTION

This invention provides for superimposing on the radiant energy from the object containing the spatial modulation of the object characteristics, a reference code in spatial form having a component which is substantially spatially invariant and a component which is spatially variant. The resulting radiation pattern is spatially coded with respect to a reference code independently of the phase or frequency of the radiation from the object and references only the spatial modulation of the wave produced by the object. More specifically, this invention provides for superimposing a shadow mask between the object and the detector or image surface where the coded pattern is to be produced, said mask having a spatially varying transparency to radiation from the object which produces a further modulation of the radiation from the object to spatially code the radiation pattern incident upon the detecting surface. An additional shadow mask having a substantially constant periodicity is positioned between the object and the image, spaced from the spatially variant mask. The resulting coded radiation pattern may be formed from radiation emanating directly from the body, such as in the case of thermal radiation in the infrared region of reradiation at a different frequency where phase coherency with the incident radiation is destroyed by the object or nuclear radiation where the energy level and/or equivalent frequency of the radiation is so high that no substantial phase characteristics at the radiation frequency can be detected or, in many instances in fact, can be found to exist. In the latter case, such spatial coding is particularly important since focusing by conventional lenses is also not, to any practical degree, possible and, hence, holography as a means of obtaining a larger effective lens aperture than a pinhole is desirable to increase the detectable energy concentration level, thereby for a given detection level and time span decreasing the amount of radiation of which the living organism being imaged must be subjected.

This invention further contemplates that a hologram may be formed by spatially coding a source of radiation which is then directed toward an object to be imaged which spatially modulates the energy and transmits such object energy to a detecting surface either by reflection, for example, in the case of conventional light energy or by transmission through the object to produce a shading modulation by the object as in the case of X-rays, and in such a case the source of radiation need not be phase coherent so that in the case of visible holography a white light or ordinary light may be used to illuminate an object or, for example, in the case of X-rays a spatially dispersed source of X-rays may be used whereas in conventional X-ray techniques, a point source of X-rays has been used to produce an X-ray image by production of the X-rays through the object to be imaged.

This invention further discloses that the spatial code preferably comprises a shadow mask which is a zone plate having a spatially variant code which is a portion of a Fresnel zone pattern.

This invention further discloses that definition of the image produced by the system of the aforementioned copending application may be further improved by further coding of the spatial pattern with a substantially spatially invariant component which produces a substantially constant spatial frequency at the detector. Such an introduction of an additional frequency, which may be considered a carrier frequency, is particularly useful when portions of a Fresnel zone plate, such as an off axis zone plate, are used to produce the code so that the spatially coded pattern at the detector plane contains only high spatial frequencies so that large objects which do not have strong spatial frequency components at high frequencies can be properly imaged. Preferably, the spatially invariant or carrier frequency is in the middle region of the detector so that the spatially variant code occurs as upper and lower side bands of the carrier. However, if desired, partial on complete suppression of one side and/or the carrier may be achieved by positioning the carrier adjacent to or above the upper limit of the spatial frequency response of the detector.

It should be noted that the foregoing invention differs from conventional holography in that the system of this invention superimposes the intensities of the code linearly while in conventional holography the amplitudes are superimposed linearly and, hence, the intensities which vary as the square of the amplitudes are superimposed nonlinearly. Since both the source intensity and the zone plate transparency are nonnegative functions, the image produced by a system using an on-axis Fresnel zone plate will contain a large average or DC value which requires a highly linear wide dynamic range detector for optimum results. This invention discloses that the DC component of the signal may be laterally displaced with respect to the axis of the system by using an axis zone plate so that the DC term may be separated either optically or by other means during reconstruction of the image. Such an off axis section, having a higher frequency average of frequency components than an on axis zone plate, is particularly useful when the additional spatial carrier frequency is introduced by positioning the spatially invariant mask, such as a half tone screen, between the object to be imaged and the zone plate.

This invention further discloses that such a system is particularly useful when an image intensifier is used directly as a detector so that in the case of X-rays, electrons are produced from a photoemissive surface as a result of X-ray impingement thereon and are accelerated to a target to produce an amplified energy level pattern thereon, or in the case of high speed nuclear particles, an intermediate region of crystal material is interposed for converting the high speed particles into a light scintillation which impinges on the photocathode to cause electron emission therefrom.

It should also be clearly understood that the large increase in effective aperture of the system makes the invention useful in many applications where the coded energy pattern is detected and recorded directly, for example on film, without additional amplification.

Also, since the informational content is in spatially coded form, local variations in the recorded information due, for example, to variations in film response or to spatial variations in photocathode sensitivity of an image intensifier or to noise generated thereby may be cancelled in the image reconstruction process.

BRIEF DESCRIPTION OF THE DRAWINGS

Other and further objects and advantages of this invention will become apparent as the description thereof progresses, reference being had to the accompanying drawings wherein.

DESCRIPTION OF THE PREFERRED EMBODIMENT

Referring now to FIGS. 1 through 4, there is shown a source of radiation 20 which is illustrated herein, by way of example only, as a thyroid gland in a person which has been rendered radioactive by administering any of the well-known radioactive pharmaceuticals to the person which have an affinity for the thyroid gland. It is to be clearly understood that any desired source of radiation can be used and that such source may be, to any desired degree, a source of spatially coherent and/or temporally coherent waves. However, since this invention does not require such spatial and/or temporal coherence, it has been found particularly useful in those cases where the spatial coherence of the radiation is low or nonexistent.

Spatial coherence as used herein means that the wave amplitude at spatially separated points has a constant phase relationship. In contradistinction, incoherent radiation, such as incoherent light, has substantially no detectable phase relationship among spatially separated points. In addition, since this invention does not rely, in its broadest concept, on temporal phase coherence, radiation of such high energy as, for example, X-rays or nuclear particles, may be imaged even though their temporal coherence is extremely short since the radiation of one photon or energy particles bears substantially no phase coherence to other particles or portions of the radiation.

Temporal coherent time duration or length as used herein means the time it takes a packet of radiation including the major portion of its associated electric and/or magnetic fields to pass a given point. Alternatively, temporal coherence length may be defined as the distance along the direction of propagation between two points where a phase coherence between portions of the wave may be detected.

Figure 3:
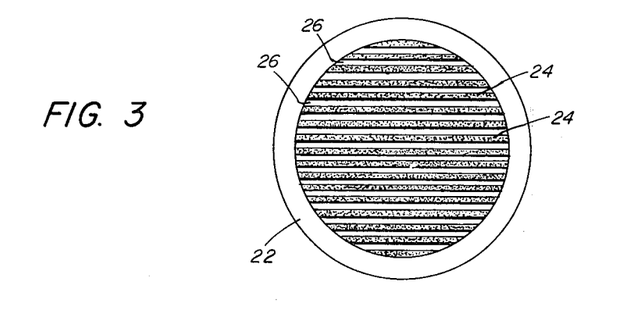
FIG. 3 illustrates a pattern of the spatially invariant half tone screen used in FIG. 1.

Positioned adjacent to radiation source 20 is a spatially periodic radiation absorbing structure 22 consisting, as illustrated in greater detail in FIG. 3, of a plurality of parallel bars 24 of material opaque to the radiation separated by spaces 26 equal in width to the width of the bars. As illustrated herein, the total open area of the mask 22 is made approximately equal to the total opaque area of the mask and may be referred to as a half tone screen. The material of the bars 24 is chosen such that the radiation from the source 20 will be absorbed if it hits the mask 22, but those portions of the radiation which are directed to the spaces 26 between the bars 24 will pass through. The resulting pattern of radiation on the opposite side of the source 20 from the mask 22 will then be a spatially coded pattern coded in accordance with a substantially periodic waveform whose amplitude immediately adjacent the mask 22 varies from zero to substantially the average intensity of the source 20 positioned behind the mask 22. While the mask 22 may be placed at various distances from the source 20, it is preferably positioned as close as convenient to the source 20, and for the purposes of this discussion will be considered as being positioned at the source 20.

Figure 1:
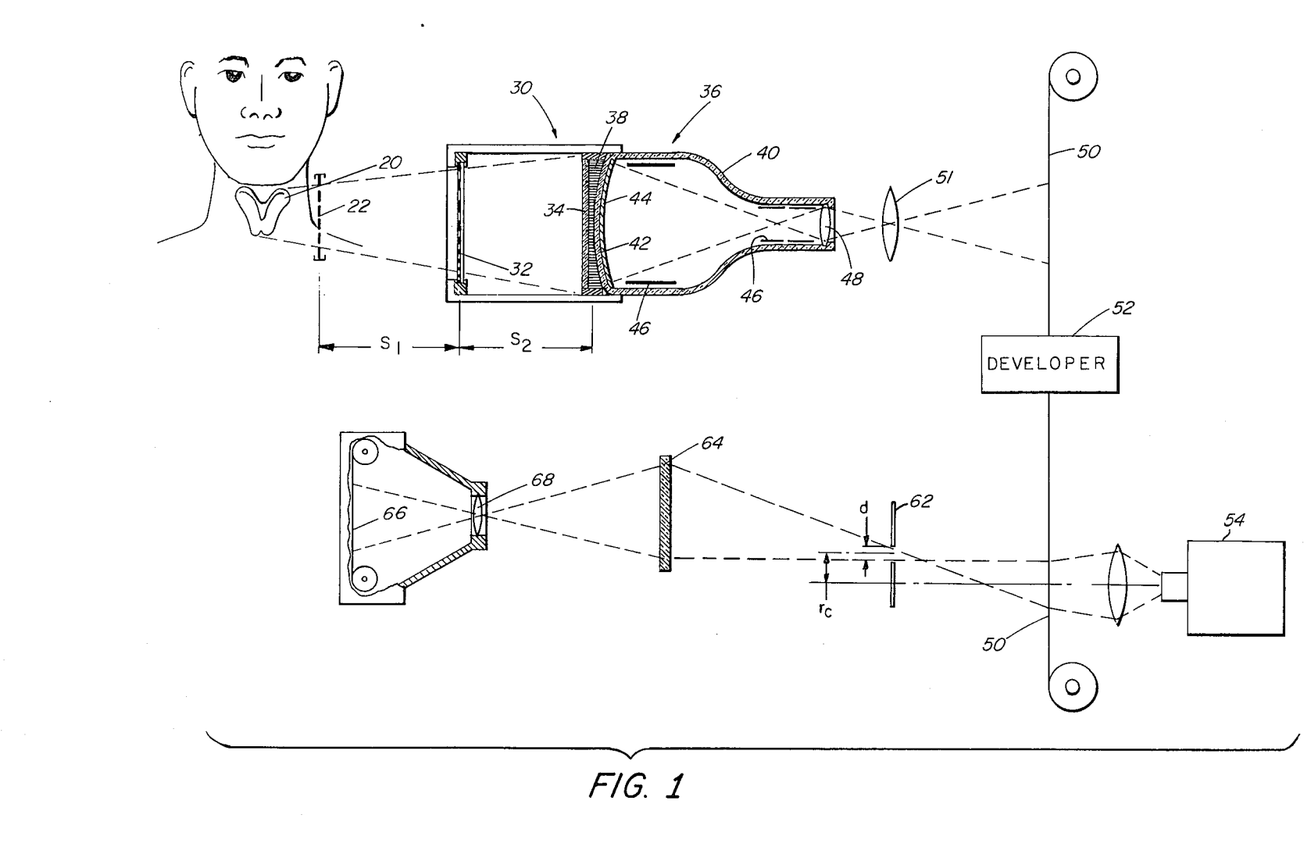
FIG. 1 illustrates a preferred embodiment of the invention.
Figure 2:
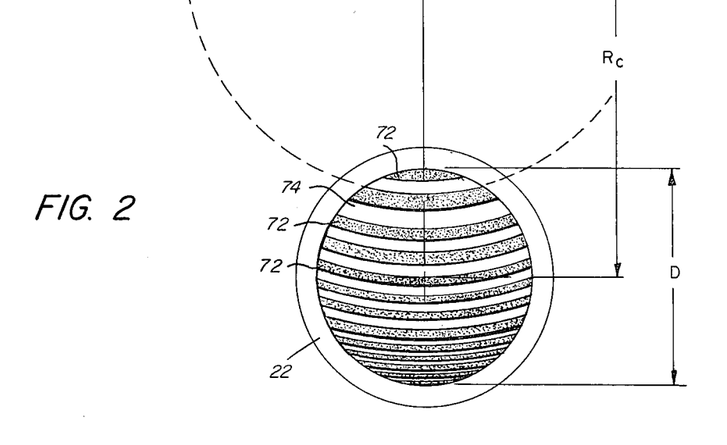
FIG. 2 illustrates a pattern of a spatially varying coded zone plate used in FIG. 1.

Positioned at a distance of, for example, a foot or two from the source 20 is a radiation detection system 30 comprising a zone plate 32 positioned at a distance $S_1$ from the source 20 and a radiation detecting crystal 34 positioned at a distance $S_2$ from the zone plate 32 and, hence, a distance of $S_1 + S_2$ from the source 20. Crystal 34 may be of any desired type, such as cesium iodide, which is responsive to the particular radiation to be detected and produces scintillations of light in response to incident radiation from source 20, which are coupled with as little dispersion as possible to a light amplifier illustrated herein as an image intensifier tube 36 coupled to crystal 34 by a fiber optics lens 38. Any desired image intensifier system can be used, such as, for example, the conventional image intensifier tube.

The image intensifier tube 36 may be, for example, a commercially available image intensifier tube, such as the X-ray image intensifier tubes 9TX, 9TB, 9TZ or 9TA manufactured by The Machlett Laboratories, Incorporated, Stamford, Connecticut, which have a nine-inch diameter input screen and an output screen of an inch or less, depending on the type. Such types introduce a power gain of several thousand, depending on operating conditions. As illustrated herein, by way of example, tube 36 comprises an envelope 40 which has a face 42 permeable to light and a photoemissive cathode 44 which emits electrons in response to scintillations of light from crystal 34. The emitted electrons are accelerated by an electric field produced by means of voltages on electrodes 46 to produce an inverted image on a fluorescent screen 48. The image on screen 48 is focused on a film 50 through a lens 51 to the amplified hologram on screen 48. Film 50 may be positioned in a conventional camera (not shown) with a lens system to focus the image produced on the fluorescent screen on the film 50 in accordance with well-known practice.

The length of time of exposure of the film 50 necessary to produce a useful hologram is a function of the intensity of the source 20, the conversion efficiency of the crystal 34 and the gain of the image intensifier 36.

Image intensifier tubes of the type disclosed herein have a resolution limited to some extent by the divergence of the light from crystal 34 as it is transferred through the fiber optics 38 and the face of the image intensifier tue and, hence, will not achieve the maximum resolution available by the grain size of a film. However, resolutions on the order of one line pair per millimeter or an order of magnitude greater than the Anger camera may be achieved. Such resolutions can be easily reproduced on the fluorescent screen 48 and the film 50 even though the size of the image on the fluorescent screen has been reduced by one order of magnitude. If desired, the image on the fluorescent screen 48 may be either reduced or enlarged by the optical lens system prior to recording on the film 50.

The film 50 is developed in accordance with well-known practice by any desired process or means indicated simply as developer 52, and the developed film may be then used to produce a reconstruction of an image of the intensity of radiation produced by various portions of the object 20. For this purpose, a source of coherent light, such as a conventional laser 54, is provided. Preferably, the beam of laser 54 is emitted from the laser output lens 56 as a diverging beam and is collimated by a converging lens 58 which directs the beam through the holographic transparence of the developed film 50. The temporally coherent substantially monochromatic beam from laser 54 is modulated by transmission through the hologram on the film 50. An iris 62 is positioned at the focal plane of the converging lens 50 which passes the desired components of the beam to form an image on ground glass screen 64, where it may be observed directly or, if desired, recorded on a film 66 by means of a lens 68 in a camera in accordance with well-known practice.

Figure 4:
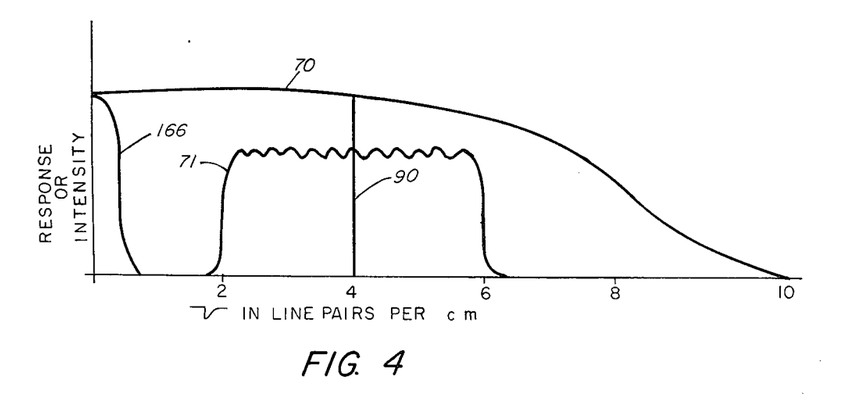
FIG. 4 illustrates a spatial frequency diagram of such components.

The preferred mode of operation of the system is as follows: The zone plate 32 is an off center section of a Fresnel zone pattern, and the half tone screen 22 is alternately opaque and transparent bars transverse to the offset direction of the zone plate 32. FIG. 4 illustrates a diagram of the spatial frequency response of the system of FIG. 1, for reasons of convenience all of the frequency responses of the various elements being referenced to the image plane which is substantially the plane containing the crystal 34. Since the crystal 34 has a finite thickness and a particle of nuclear energy can produce a scintillation of light at any position through the thickness, degradation of definition of the reconstructed images occurs with thicker crystals producing more light but with less definition. In general, crystal 34 is reduced in thickness as far as possible while still retaining sufficient conversion efficiency to produce useful images. For example, if a cesium iodide crystal is a centimeter thick, it will convert to light the major portion of those nuclear particles impinging upon it and, hence, will have substantially its maximum conversion efficiency, thereby resulting in maximum system sensitivity. However, if the thickness of crystal 34 is, for example, one millimeter, it will still convert a substantial portion of the nuclear particles impinging thereon to light, and the remainder will simply proceed through the equipment to be absorbed without production of light. Since the system has substantial amplification, relatively thin crystals may be used. However, it should be noted that any diminution in sensitivity requires either an increased concentration of the radioactive pharmaceutical to be administered to the patient or a longer period of time for exposure of the film 50 incident to which extraneous noise effects or movements by the patient can also reduce definition.

It may further be noted that additional expedients for improving definition, such as forming the crystal in the shape of small light tubes a millimeter or so in diameter which have light reflecting walls such that any light generated by a nuclear particle in a light tube would be directed toward the cathode 44, could be substituted for the solid crystal 34 plus fiber optics lens 38. Alternatively, the crystal 34 could be positioned a substantial distance from the image intensifier 36 and a focusing lens positioned therebetween. Such a lens, which could be, for example, of the flat or Fresnel type, should be chosen for the maximum depth of field so that light from all regions of the crystal could be relatively sharply focused on the cathode 44.

The frequency response curve of FIG. 4, as projected to the effective image plane at crystal 34, is indicated, by way of example, as a spatial frequency response curve 70. The frequency $v$ is plotted in line pairs per millimeter and has a high frequency cutoff, for example, limited by the degradation of the light coupling system involving the thickness of crystal 34, the fiber optics system 38 and the thickness of the envelope face 42 on which the photocathode 44 is superimposed. Such frequency response is indicated here, by way of example only, as those wavelengths producing a spatial definition of slightly greater than two line pairs per millimeter. This means that the shadow pattern of lines spaced apart by substantially less than a millimeter cannot be distinguished from each other.

Without the constant periodicity mask 22, the lower frequency response corresponding to longer wavelengths would be limited by the pattern projected by the zone plate 32 as shown by curve 71. For example, if $S_1$ equals $S_2$, energy from a point in object 20 projects space 74 on crystal 34 with twice its width. The size of the projection of the plate 32 on crystal 34 is magnified by the factor $S_1+S_2/S_1$. Therefore, if the image plane at crystal 34 has a diameter of 24 centimeters and $S_1 = S_2 = 15$ cm and the largest space 74 of plate 32 is 0.125 centimeters wide, its point source projection on crystal 34 will be 0.25 centimeters wide and the lower frequency response limit will be two line pairs per centimeter. Similarly, the smallest spacing 75 is about 0.04 centimeter resulting in an upper frequency response of about six lines per centimeter.

Addition of the screen 22 with a bar spacing of four bars per centimeter projects a carrier frequency of four lines per centimeter to the image plane as shown by line 90. Frequency components of the object then appear as upper and lower modulation side bands on either side of carrier frequency 90, with the lower frequencies being nearer the carrier frequencies. The higher object frequencies recorded in the hologram are then limited by the upper and lower cutoff frequencies of the mask 32 as shown by curve 71. Varying the offset distance $R_c$ shifts the position of curve 71, and varying the diameter D of the mask 32 varies the bandpass of curve 71. As an example, the object 20 may produce gamma rays having an energy of around 140 KEV by using technecium, and the mask 22 may be lead or gold .3 millimeter thick and the mask 32 may be gold .3 millimeter thick.

It should be pointed out that the projection of the pattern from a point source at a fixed distance beyond zone plate 32 on the crystal 34 may be enlarged or reduced by movement of the crystal 34 toward and away from the zone plate 32, that is, by varying the distance indicated as $S_2$ in FIG. 1. A similar variation can be achieved by varying the distance from the object 20 to the zone plate 32. Thus, the spatial frequency response of the system may be varied by varying either or both of these two distances. Because the distances from different points on the object 20 to the zone plate 32 differ, information is recorded in the hologram from which images of any of a series of slices of the object may be reproduced.

The off-center section of a Fresnel zone pattern results in a hologram in which separation of the positive and negative images from the DC component can be achieved. This occurs by reason of the fact that the hologram formed, for example, on the film diffracts the projected light toward the axis of the Fresnel zone and thus in the reconstruction, three discs of light are projected to the plane of the iris 62, one corresponding to the real image, one corresponding to the virtual image and one corresponding to the substantially steady state or noise component of the signal. Such patterns are diffracted different distances with respect to the axis of the Fresnel zone plate and, hence, are separated with their centers lying along a line displaced in the same direction as the axis of zone plate 32 is displaced from the center of the Fresnel zone pattern. Such off-centering thus improves the reconstruction to reproduce an image of the object 20 on the screen 64 from which the DC or background component and one of the two images have been blocked by the iris 62 while permitting the other image to project through the aperture in iris 62. The aperture size of iris 62 is preferably large enough to permit all the components of the desired image to pass through since the undesired component, for example indicated by the ray pattern 78 in FIG. 1, will be displaced from the desired pattern 80 by a lateral distance substantially greater than the aperture size necessary to pass the desired portion of the pattern. The half tone 22, which for purposes of explanation will be considered substantially in the plane of the object 20, is chosen to have a width of the spaced parallel bars 24 equal to the spaces 26 between the bars. The resultant radiation pattern passing through screen 22 corresponds to a spatial frequency. Preferably, a particular orientation of the bars 24 with respect to the offset line of the zone plate 32 is maintained. For example, as illustrated herein, the bars 24 of the screen 22 are positioned transverse to the line between the center of the Fresnel zone pattern from which the zone 32 is formed and the center of zone plate 32. Since this offset line, as projected to the image plane is the line about which the zone plate 32 is symmetrical, the pattern projected by the half tone screen 22 to the image plane is oriented to be symmetrical about this line.

The size and periodicity of the spatial pattern projected on the crystal 34 by the screen 22 is a function of the spacing of the bars 24 and the distance of the screen 22. The screen 22 may be regarded as at a distance from the object 20 which is sufficiently small compared to the distance between the object 20 and the crystal 34 that screen 22 is substantially in the plane of the object, and the object may then be regarded as a series of closely spaced objects emitting radiation. Thus, since the spacing is uniform, producing a periodically repetitive spatial wave, this periodicity may be regarded as a spatial carrier frequency whose amplitude is modulated from zero to a peak, depending on the radiation intensity of the particular portion of the object directly behind a given opening in the screen 22.

It should be noted that the carrier frequency is particularly important for the lower spatial frequencies of the object which might otherwise fall outside the response curve 71 and which are by this process transferred within the response curve.

Since the patterns produced at the image plane by the zone plate are components of the radiation from the source containing the carrier frequency modified with the zone plate characteristics, a multiplication function and, hence, modulation of the carrier is achieved. As a result, spatial side band frequencies are produced at wavelengths both above and below the carrier frequency spatial wavelength. The lower modulating frequencies of the object distribution modulated on the carrier are closest to the carrier and the higher frequencies are farther from the carrier.

While the carrier frequency 90 is indicated as falling within the response band of the zone plate, it can, if desired, be selected as a frequency above that to which the zone plate will respond. Such a system may be then considered to be a single side band suppressed carrier system and will exhibit the inversion of the side band with the higher spatial frequencies of the zone plate 22 lying adjacent the lower frequency end of the spatial response curve of the detector. A reconstruction of a hologram in which the carrier and/or one side band have been suppressed may be used for enhancement of certain features of the object such as, for example, those having high frequency components.

In the above-described system, a particular nuclear energy particle from object 20 produces a scintillation of light at a particular location in crystal 34 which radiates from crystal 34 for a short period of time after crystal 34 is excited by said nuclear particle. The total quantity of useful light may, if desired, be increased by placing a silver reflecting surface 96 on the side of crystal 34 nearest the zone plate 32 so that light emanating from a point source of crystal 34 traveling in the opposite direction from the image intensifier 36 will be reflected by the reflecting surface 96 of crystal 34. Under these conditions, however, such reflected light will include components impinging on reflector 96 at a variety of angles with respect to the surface of reflector 96, hence somewhat degrading the spatial frequency response of the system since the effective spot size in the crystal 34 seen by the image intensifier 36 will increase. If desired, further increases in definition may be achieved by forming crystal 34 as a series of tubes, for example, a millimeter in diameter, and bonding the tubes together to make a fiber optics plate with a bonding medium having an index refraction substantially different from that of the crystal material 34 so that substantially all the energy radiated from a point in one of the tubes energized by a high speed nuclear particle will be directed along the axis of the tube due to reflection at the surface of the tube. If desired, each of the tubes may be individually coated with reflective material prior to bonding together, and the reflective layer 96 may be applied to the ends of the tubes closest to the object 20. If desired, this assembly may be positioned inside the evacuated space of the envelope 40 and the photocathode 44 positioned directly on the ends of the tubes, in which case the photocathode is made up of a layer of transparent conductive material and a layer of photoemissive material in accordance with well-known practice.

Figure 5:
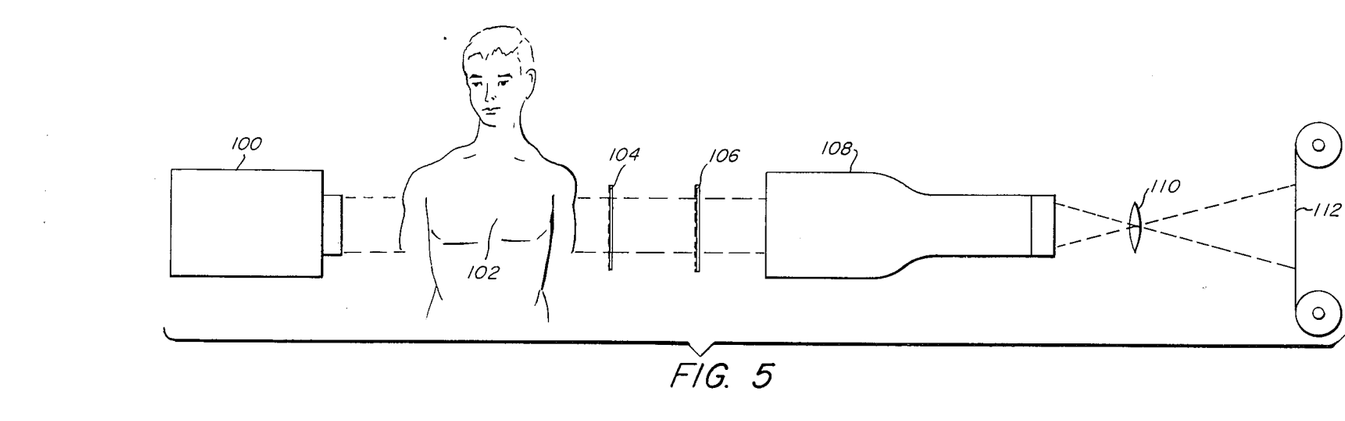
FIG. 5 illustrates a further embodiment of the system wherein an X-ray image may be produced.

Referring now to FIG. 5, there is shown a further embodiment of the invention wherein a large-area X-ray source 100 emits X-rays through an object 102, a spatially periodic mask 104 and a spatially varying zone plate 106 to image intensifier 108 of the type shown in FIG. 1 to produce a hologram on a film 112 through a lens system 110. Since the X-ray source 100 is used to project a pattern through the object 102 and since the focusing of the X-rays is not in and of itself necessary for the production of an image of the object 102, the definition of the final image will not be degraded by using a large diameter X-ray source. In contradistinction, a conventional X-ray picture requires that the X-ray source be substantially a point source so that its intensity is limited by the beam striking a point on a target producing the X-rays. The more intense the beam, the hotter the target area. If, on the other hand, the X-ray source is produced from a defocused electron beam striking a large target area, localized heating of the target electrode is substantially reduced and more intense X-ray sources may be produced. Since the beam of X-rays from the source 100 is coded by shading from the half tone screen 104 and the zone plate 106, the object 102 may be regarded as a source similar to the source 20 of FIG. 2 radiating energy in any of a plurality of directions. Such energy is coded by similar considerations to those illustrated in connection with FIG. 1 and the same spatial frequency considerations apply. The hologram so formed may be reconstructed in a similar fashion to that illustrated in FIG. 1.

The masks 104 and/or 106 may, if desired, be positioned in any order between the source 100 and the object 102 by selection of the appropriate mask aperture sizes thereby reducing the high energy dosage through the body 102.

Figure 6:
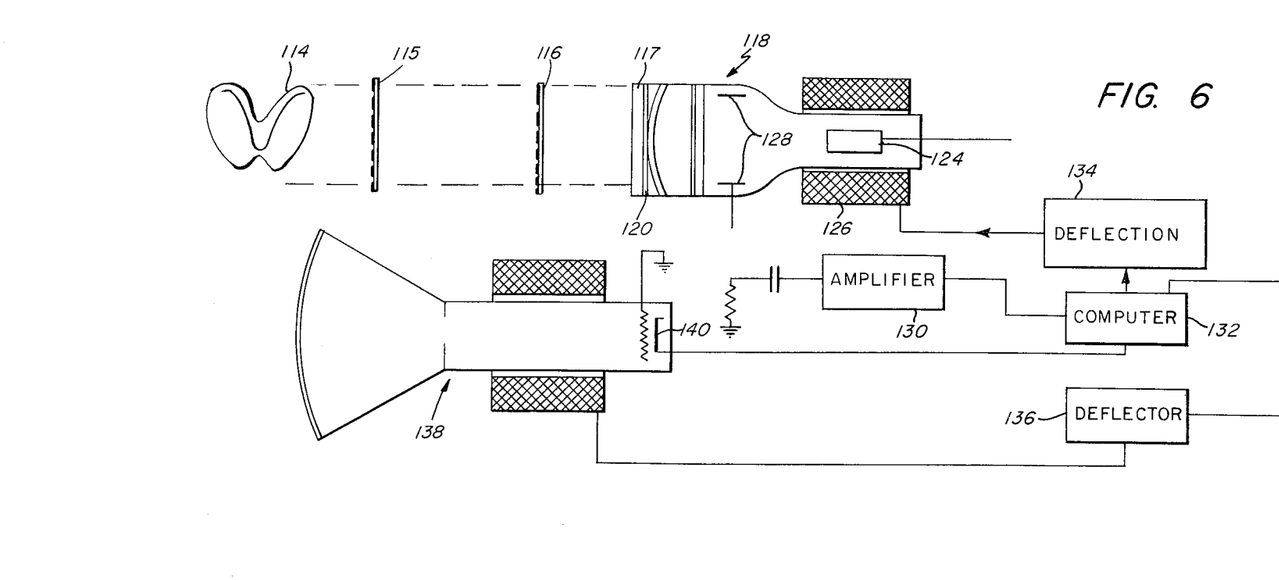
FIG. 6 illustrates a further embodiment of the system wherein the image may be viewed directly.

Referring now to FIG. 6, there is shown a still further embodiment of the invention in which an object 114 produces a spatially distributed pattern of incoherent radiation either as particles forming a radioactive component or as a shading of an X-ray image from a source (not shown) illuminating the object 114. A half tone mask on screen 115 introduces spatial carrier frequency, and a zone plate 116 produces spatial position coding of the radiation which is detected by crystal 117 positioned on the face of a camera pickup tube 118 which may be of the type wherein a photocathode layer 120, upon which scintillations of light from crystal 117 fall, emits electrons which under the influence of an electric field are directed to a target 122 which may be, for example, of semi-conductor material such as silicon which produces a large number of electron-hole pairs when struck by a high speed electron. For example, if the target 122 is maintained positive with respect to the photocathode 120 by a voltage of several thousand volts, several thousand electron-hole pairs may be generated in the target 122 for each electron emitted from photocathode 120. Such electron-hole pairs are used to discharge a layer of electrons which are deposited on the surface of target 122 opposite to the photocathode 120 by means of a conventional heated cathode 124 producing a focused beam which is swept across the target 122 by means of a deflection coil system 126 in accordance with well-known practice. The voltage of cathode 124 is maintained at a small voltage, for example several volts negative, with respect to the target 122 so that in those regions where electrons from the photocathode 120 impinge on the target 122 and discharge the voltage across the target, electrons from the cathode 124 will recharge the target 122 and in those regions where the target 122 remains fully charged, the electrons from cathode 124 will be reflected and collected by a collecting electrode structure 128 which feeds a signal to an amplifier 130 and thence to a computer 132 which may be used to introduce a spatial correction for any spatial distortion introduced by the camera pickup tube 118. For this purpose, the deflection system 134 is synchronized with signals from the computer so that the position or address of the beam from cathode 124 on the target 122 produces an address deflection for an output display system which may, if desired, have added thereto a correction derived from a read-only memory for the spatial distortion introduced by the camera tube 118. Computer 132 may produce the inverse correlation required to reconstruct an image directly, in which case the signal deflection out to a deflection system 136 driving the deflection coils of a display tube 138 may be of any desired shape, such as a conventional television raster, and the signal fed from the computer to the intensity modulation system of the tube 138, such as to the cathode 140, will produce the reconstructed image on the fluorescent screen 142 of the tube 138.

Such a computer program reconstructing process may, if desired, store the holographic image digitally as a hologram and perform the necessary correlation functions to reconstruct the image by convolving a recorded hologram with the functions derived from the spatial patterns of the zone plate 114 and screen 112 and stored digitally in a memory in the computer 132. Alternatively, the computer may be programmed to produce on the screen 142 an image of the hologram sufficiently amplified to produce a clear picture and with the spatial distortion in the system corrected by algebraically adding to each deflection position of the deflection system 134 the necessary correction factors for the deflection system 136, such a deflection system correction being previously stored in a memory in the computer.

It should be noted that since the information produced by the holograms generated in accordance with this invention contains depth information, any given distance slice of the object may be reproduced from the holographic information, for example, by varying the position of the ground glass screen 64 with respect to the film 50 in FIG. 1 or by changing the reconstruction program of the computer 132 of FIG. 5 so that once the hologram is recorded either on the film or in a computer memory, any of a number of slices of the object may be displayed so that the effects of three-dimensional observation of the object may be obtained.

From the foregoing, it is believed apparent that where weak signals are to be detected from a spatial pattern of radiation, such signals may be formed in a hologram and amplified in that form. As a result, extraneous noise background in which such signals normally occur produces a generally constant average output signal which cancels in the system permitting high amplification of the desired signal.

Figure 7:
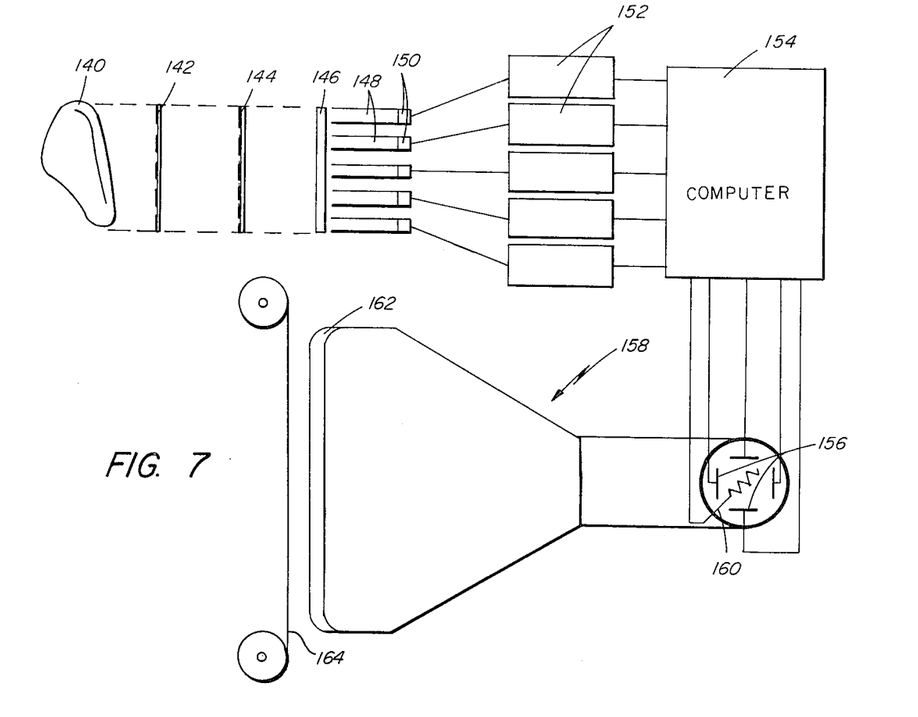
FIG. 7 illustrates a still further embodiment of the system wherein amplification is not required for recording a hologram.

Referring now to FIG. 7, there is shown a further embodiment of the system wherein an object 140 has a half tone or carrier injection screen 142 equivalent to the screen 22 of FIG. 1 positioned adjacent the object which may be, for example, a thyroid gland which has absorbed a radioactive pharmaceutical. A spatially coded zone plate 144 is positioned between screen 142 and a crystal 146 which converts nuclear particles into light scintillations. Light from crystal 146 is captured by light tubes 148 positioned on the opposite side of crystal 146 from the screen 144, the portion of the light entering each of the tubes 148 being determined by the location in the crystal 146 producing the light scintillation. Light entering the tubes 148 is detected by photodetectors 150 amplified by amplifiers 152 whose outputs are fed to a computer 154. In its simplest form, computer 154 may be a resistive matrix having deflection voltage outputs shown here diagrammatically as feeding vertical and horizontal deflection plates 156 of a cathode ray tube 158, the summation of the intensities of the outputs of amplifiers 152 being used to feed a control electrode, such as the grid 160 of the tube 158, such that a bright spot occurs on a fluorescent screen 162 of the cathode ray tube 158. The location of the spot on the screen 162 corresponds to the relative location of the scintillation of light emanating from crystal 146. The details of such a camera and display structure are conventional and have heretofore been used to produce nuclear images from a source 140 with a conventional pinhole or collimator.

In accordance with this invention, the image formed on the fluorescent screen 162 comprises a hologram with spatial distortion due to the system preferably reduced to a minimum. This may be accomplished in this case by introducing correction factors in the computer 154, for example, by digitalizing the positional inputs from the amplifiers 154 to determine X and Y locations and reading a particular correction factor in a memory in the computer corresponding to that location which is added to the deflection signal supplied to the deflection plates of the cathode ray tube 158.

The holographic image thus formed may be, for example, recorded on a film 164 which is then developed and the image thereon reconstructed in accordance with the system illustrated at FIG. 1.

In accordance with well-known practice, the detection system comprising the crystal 146 may be made to have a gain of several thousand so that each particle of nuclear energy produces a spot of light on the fluorescent screen 162. The spatial discimination corresponding to the upper spatial frequency in such a system is limited by the number of individual photodetectors and, as shown here, the system may have, for example, five detectors across a diameter so that a pattern of detectors has one detector at the center, six detectors in the first ring and twelve detectors in the second ring. Such a camera having a diameter of on the order of twenty centimeters may with interpolation have a spatial frequency discrimination somewhat better than 0.5 line pairs per centimeter. By adding additional rings and forming a larger camera, additional discrimination may be achieved so that spatial frequency discriminations of a few millimeters are possible. Such a camera, in addition, exhibits a somewhat greater depth of field of the crystal 146 than the image intensifiers of FIG. 1 since a scintillation of light in the crystal 146 tends to radiate, to a first order of approximation, corresponding quantities of light to the light tubes 148, whether it is positioned adjacent the surface of the crystal closest to the light tubes, the center of the crystal, or the surface of the crystal furthest from the light tubes. Additionally, a reflecting surface may be applied to the crystal 146 on the side thereof opposite to the light tubes, and by an estension of the above reasoning, this appears to make the crystal approximately twice as thick but the total light received by the light tubes is computed to determine a location across the face of the crystal 146. Thus, it may be seen that for those instances where the higher energy nuclear particles are used and a relatively thick crystal, for example of several millimeters thick, is used, the detector of the type shown in FIG. 7 will be comparable in definition to that shown in FIG. 1. However, in the relatively low energy nuclear particles and most X-rays, the system illustrated in FIG. 1 is capable of substantially greater spatial definition than that of FIG. 7. For example, the upper frequency cutoff of the system shown in FIG. 7 is illustrated as curve 166 in FIG. 4, and the frequencies of masks 142 and 144 are adjusted to project carrier and bandpass frequencies falling within curve 166.

The considerations with respect to frequency response produced by the periodic screen 142 and the zone plate 144, which were set forth for FIG. 1, may be used to derive the proper spacings for the half tone screen 142 and the pattern of zone plate 144.

While the embodiments illustrated herein use an off-center section of a Fresnel pattern for the zone plate and a square mesh pattern, any desired pattern may be used for the mesh 142 and the zone plate 144. For example, the bars of plate 142 could be replaced by a plate in which a periodic pattern of holes is formed, said holes being round, elliptical, triangular or any other desired shape. In addition, the relative positions of the zone plate 144 and screen 142 are by way of example only, and holographic patterns from which images may be formed are obtained with other positions of the plates.

Figure 8:
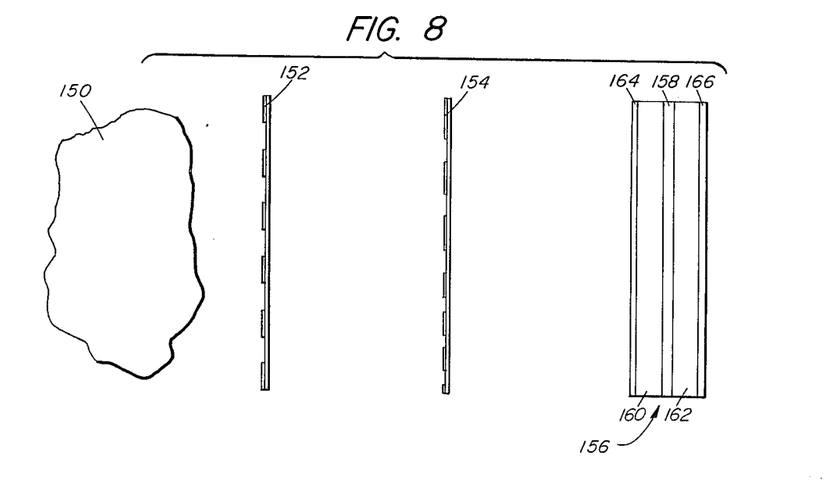
FIG. 8 illustrates alternative patterns for zone plates and spatially periodic filters.

Referring now to FIG. 8, there is shown a further embodiment of the invention wherein amplification prior to recording of the signals derived from the high energy particles has been eliminated. Such amplification has been found to be unnecessary in certain applications where either the intensity of the particles from the object or the time duration of exposure or a combination of both will produce sufficient total energy at a recording system to produce a holographic record. This is possible largely because the use of a coded zone plate increases the effective aperture of the detecting and recording system by several orders of magnitude and, hence, increases the total energy per unit time available at the film. More specifically, there is shown a body 150 of high energy particles. Such a body may be a body of living tissue similar to the thyroid gland illustrated in the previous embodiments or any other desired material, organic or inorganic, or it may be a body through which high energy rays such as X-rays are projected from a dispersed source. Positioned adjacent to body 150 is a periodic mask 152 which may be of the type illustrated in FIG. 3, and spaced from mask 152 is a varying periodicity mask 154 which may be of the type illustrated in FIG. 2. It is to be clearly understood that any other means of coding the energy from the body 150 is spatial form may be used, if desired. A detector-recorder 156 is spaced from the varying periodicity mask 154 by the same distances disclosed in connection with the operation of FIG. 1. Detector 156 comprises a film 158 sandwiched between two layers of crystals, such as calcium tungstate, 160 and 162 which convert the high energy particles into light. Light reflecting surfaces 164 and 166 are applied to the surfaces of crystals 160 and 162 on the opposite sides from those surfaces in contact with the film 158. Particles from the source 150 which strike the detector 156 are converted into scintillas of light either in the crystal 160 or the crystal 162. Thus, the effective light-energy-converting thickness of the detector 156 is the total thickness of the crystals 160 and 162 whereas the average intensity spot size produced by a particle in detector 156 will be substantially less than if the film had been positioned behind the combined thicknesses of crystals 160 and 162. The reflecting surfaces 164 and 166 are used to reflect light produced by the crystals 160 and 162 which travel in all directions in the crystal 162. It should, of course, be clearly understood that light traveling through the crystal 162 in a direction parallel to the film can be absorbed by additives after a relatively short distance through the crystal.

The film 158, after exposure in the detector 156, is removed therefrom, and the image of the object is developed, reduced in size photographically and reproduced in the same fashion as that shown in FIG. 1. Such a system has the advantage that for a given crystal thickness there is no substantial additional degradation of the recorded image by the amplification system. For example, by making the crystals a half millimeter in thickness, a definition on the film in excess of two line pairs per millimeter can be achieved. In addition, since there is no distortion of the image during the amplification process, degradation of the reproduced image due to such distortion may be substantially reduced. In addition, such a system for producing photographic holograms is substantially less expensive than those using an amplifier system, thereby making such equipment available to market areas which cannot afford the more expensive equipment.

This completes the description of the specific embodiments of the invention disclosed herein. However, many modifications thereof will be apparent to persons skilled in the art. For example, the zone plate and/or half tone screen have their surfaces other than parallel to the crystal surface 146 and/or their surfaces may be curved to add second order corrections to the overall system or for other purposes. In addition, while the invention illustrated herein is particularly applicable to those areas where temporal noncoherent sources of radiation of low intensity are to be detected, the invention is also applicable where the sources of radiation are at least partially coherent as in visible light or infrared light either in space or in time as well as to substantially noncoherent sources of radiation in the infrared spectrum, and the principles of this invention may be applied to the detection of sound waves radiated, for example, through an aqueous medium. Also, one or more elements of the system may be moved with respect to the others during the radiation detecting process as in certain radar systems while still achieving the periodic coding and the spatial position coding of this invention. In addition, any desired shape, size and/or number of apertures may be used for the zone plate and carrier injection mask, the illustrations of FIGS. 2 and 3 being by way of example only and as shown are less than the 100 or so bars or arcuate members actually used for 12 cm. diameter plates used as members 22 and 32 to produce the frequency characteristics illustrated in FIG. 4. Accordingly, it is contemplated that this invention be not limited by the particular details of the embodiments illustrated herein except as defined by the appended claims.

What is claimed is:

1. The method of forming an image of the locations of a radiopharmaceutical introduced into a body of living tissue comprising the steps of:
   introducing said radiopharmaceutical into said body of living tissue;
   deriving informational signals from said high energy particles which are indicative of the location of emission of said particles from said body which have a spatial reference code having a varying periodicity portion and a substantially constant periodicity portion; and
   deriving from said signals an image of the points in said body of living tissue from which said high energy particles have emanated.

2. The method in accordance with claim 1 wherein said informational signal deriving step comprises spatially detecting at least a portion of said high energy particles which pass through a spatially coded mask.

3. The method in accordance with claim 2 wherein said mask selectively absorbs certain of said particles with a spatially varying periodicity.

4. The method in accordance with claim 3 wherein said signal deriving step comprises converting the energy level of said high energy particles to radiation of a lower intensity than the intensity of said particles.

5. The method in accordance with claim 1 wherein said step of deriving said image comprises directing a beam of substantially coherent light through a pattern derived from said informational signals.

* * * * *

UNITED STATES PATENT OFFICE
CERTIFICATE OF CORRECTION

Patent No. 3,961,188            Dated June 1, 1976

Inventor(s) Harrison H. Barrett

It is certified that error appears in the above-identified patent and that said Letters Patent are hereby corrected as shown below:

Column 2, line 28, change "of" to -- or --

Column 2, line 41, change "of" second occurrence to -- to --.

Column 3, line 32, after "an" insert -- off --

Column 5, line 34, change "types" to -- tubes --

Column 5, line 58, change "tue" to -- tube --

Column 8, line 34, between "zone & 32" insert -- plate --

Column 12, line 50, change "estension" to -- extension --

Column 13, line 41, change "is" to -- in --

Signed and Sealed this

Twenty-sixth Day of October 1976

[SEAL]

Attest:

RUTH C. MASON
Attesting Officer

C. MARSHALL DANN
Commissioner of Patents and Trademarks